US012331135B2

(12) United States Patent
Na et al.

(10) Patent No.: US 12,331,135 B2
(45) Date of Patent: Jun. 17, 2025

(54) ANTI-TYROSINASE ANTIBODY FOR INHIBITING TYROSINASE AND USE THEREOF

(71) Applicant: HAUUL BIO, Chuncheon-si (KR)

(72) Inventors: Hee-Jun Na, Chuncheon-si (KR); Yun-Suk Lee, Chuncheon-si (KR); Je-Ok Yoo, Chuncheon-si (KR); Kwang-Soon Lee, Chuncheon-si (KR); Kang Seung Lee, Chuncheon-si (KR); Seung Je Min, Chuncheon-si (KR)

(73) Assignee: HAUUL BIO, Chuncheon-si (KR)

( * ) Notice: Subject to any disclaimer, the term of this patent is extended or adjusted under 35 U.S.C. 154(b) by 878 days.

(21) Appl. No.: 17/613,121

(22) PCT Filed: Dec. 13, 2019

(86) PCT No.: PCT/KR2019/017719
§ 371 (c)(1),
(2) Date: Nov. 22, 2021

(87) PCT Pub. No.: WO2021/025239
PCT Pub. Date: Feb. 11, 2021

(65) Prior Publication Data
US 2022/0213220 A1    Jul. 7, 2022

(30) Foreign Application Priority Data

Aug. 8, 2019  (KR) .................. 10-2019-0096864

(51) Int. Cl.
*A61P 17/02*    (2006.01)
*A61K 8/64*    (2006.01)
*A61Q 19/02*    (2006.01)
*C07K 16/40*    (2006.01)

(52) U.S. Cl.
CPC .............. *C07K 16/40* (2013.01); *A61K 8/64* (2013.01); *A61P 17/02* (2018.01); *A61Q 19/02* (2013.01); *C07K 2317/565* (2013.01); *C07K 2317/622* (2013.01); *C07K 2317/76* (2013.01); *C07K 2319/30* (2013.01)

(58) Field of Classification Search
CPC ............ A16P 17/02; A61K 8/64; A61Q 19/02
See application file for complete search history.

(56) References Cited

U.S. PATENT DOCUMENTS

| 5,843,674 A | 12/1998 | Takimoto et al. |
| 5,962,417 A | 10/1999 | Gilchrest et al. |
| 2009/0053707 A1 | 2/2009 | Yaar et al. |
| 2010/0158927 A1 | 6/2010 | Reiter et al. |

FOREIGN PATENT DOCUMENTS

| CN | 1465696 A | 1/2004 |
| CN | 101360761 A | 2/2009 |
| JP | 08-231599 A | 9/1996 |
| KR | 10-2000-0005059 A | 1/2000 |
| KR | 10-2009-0041909 A | 4/2009 |

OTHER PUBLICATIONS

International Search Report for PCT/KR2019/017719 mailed May 7, 2020 from Korean Intellectual Property Office.

*Primary Examiner* — Mark Halvorson
*Assistant Examiner* — Dennis J Sullivan
(74) *Attorney, Agent, or Firm* — Revolution IP, PLLC

(57) ABSTRACT

The present invention relates to an anti-tyrosinase antibody for inhibiting tyrosinase and use thereof, and more particularly, to an anti-tyrosinase antibody including a heavy chain CDR and a light chain CDR of specific sequences, or an antigen-binding fragment thereof. The anti-tyrosinase antibody is expected to be effectively utilized for improving skin whitening or treating skin pigmentation disorders by inhibiting tyrosinase activity.

4 Claims, 3 Drawing Sheets
Specification includes a Sequence Listing.

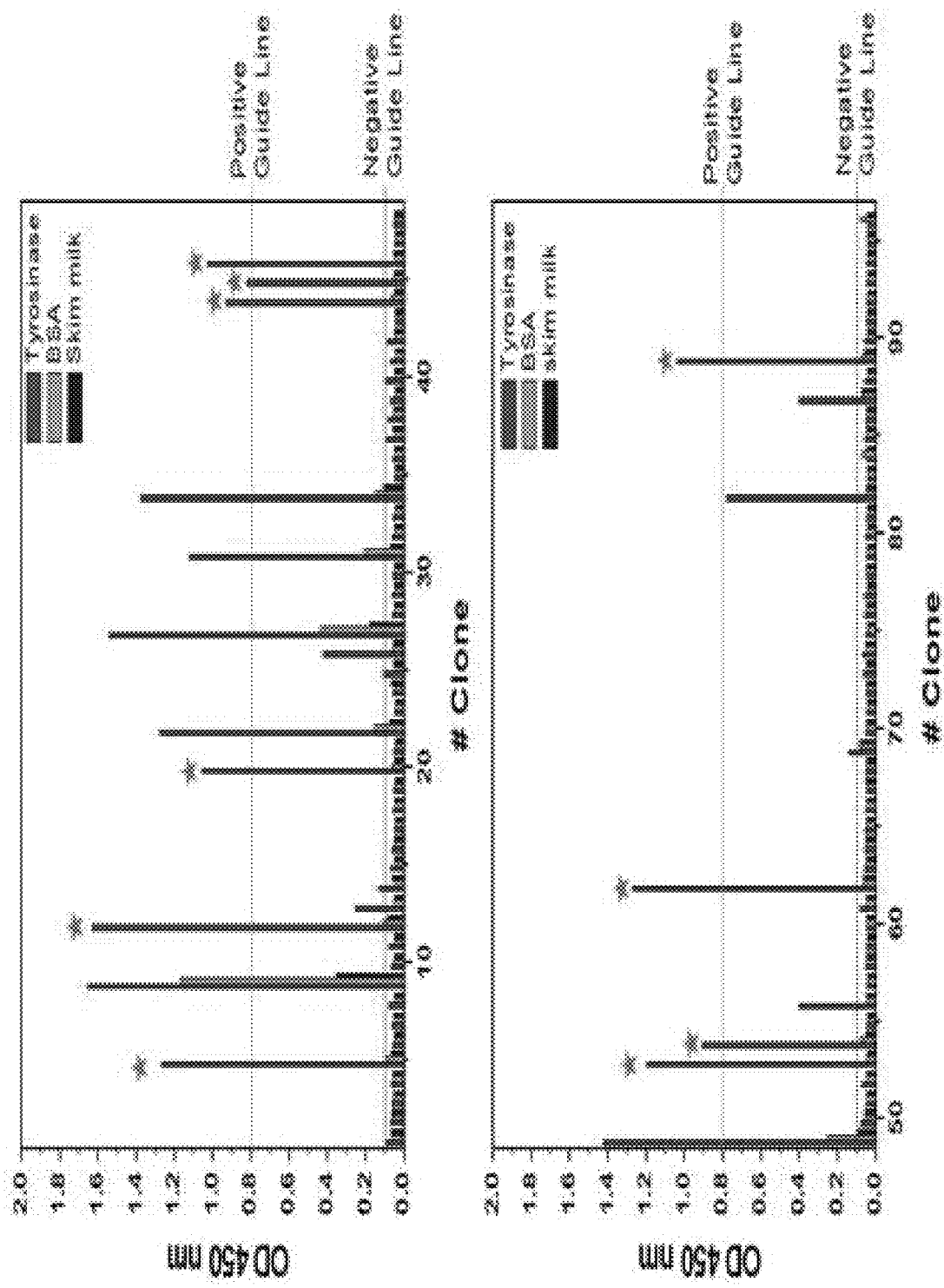
[FIG. 1]

[FIG. 2]
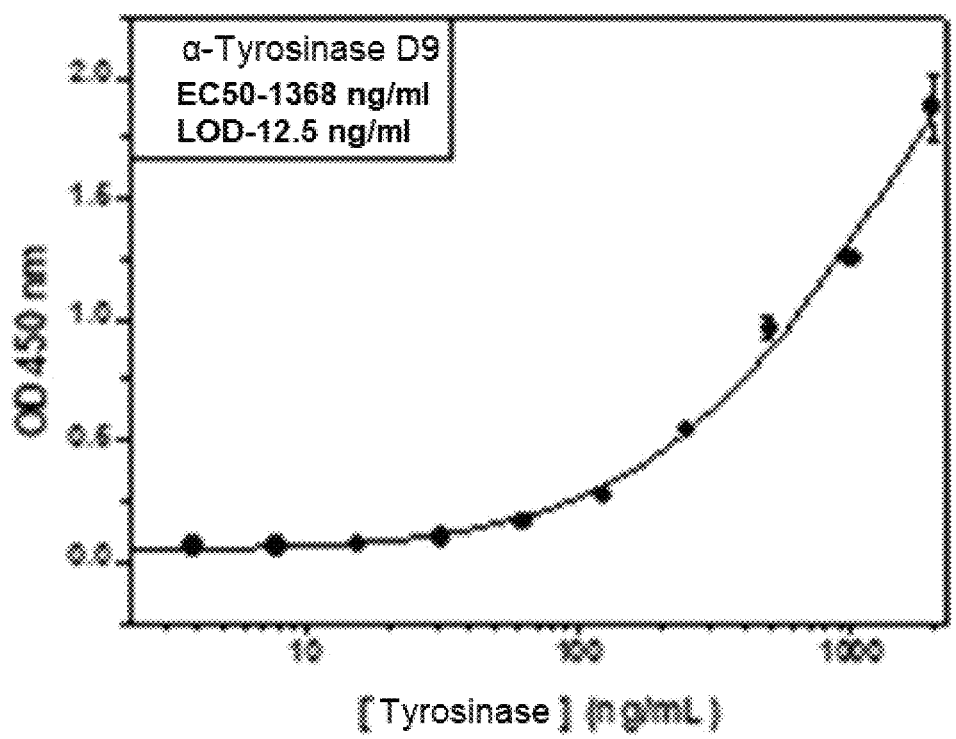
[FIG. 3]
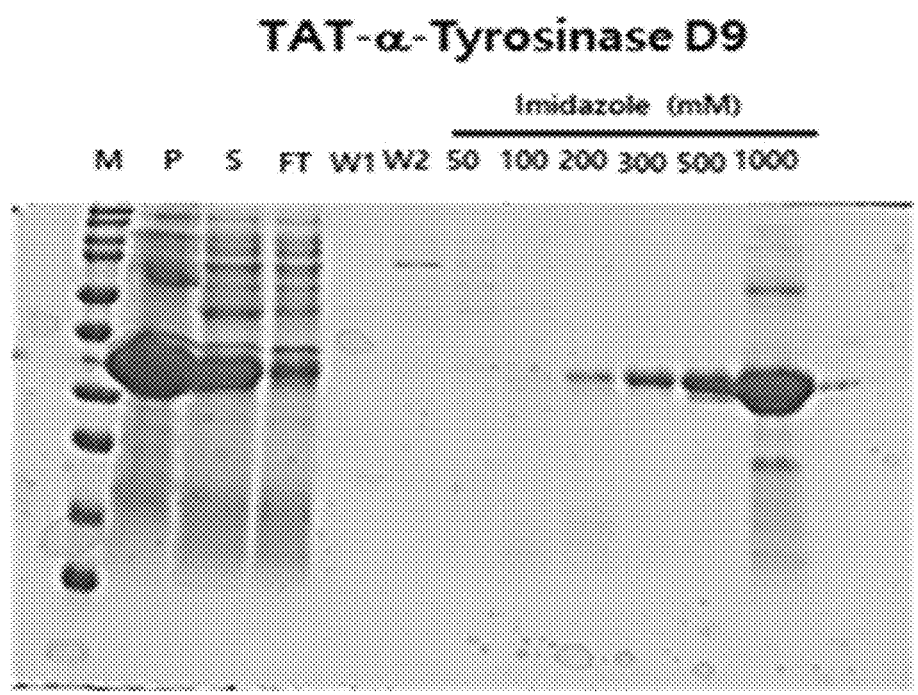

[FIG. 4]
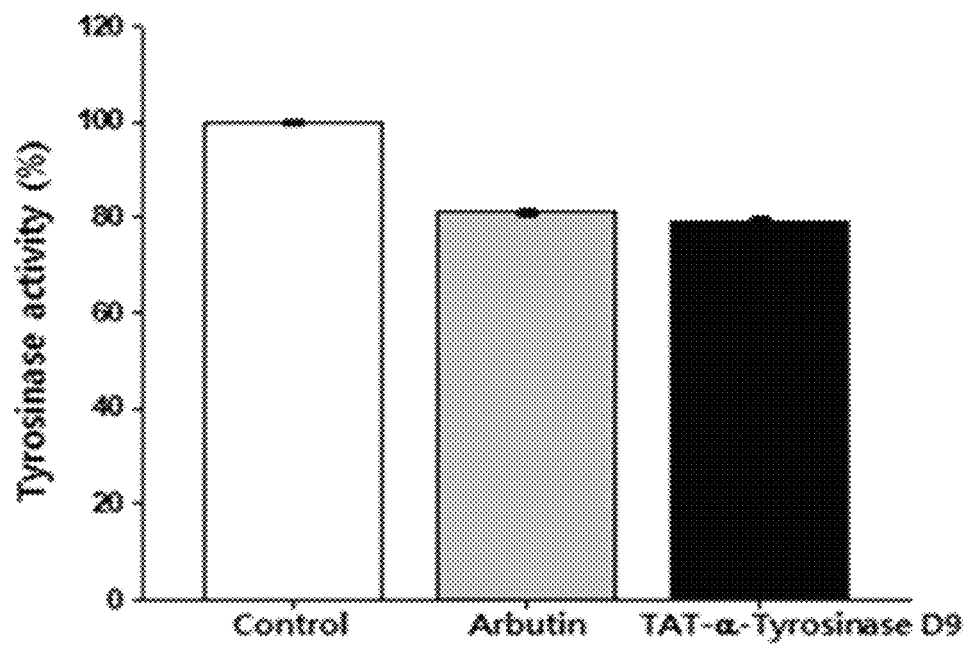
[FIG. 5]
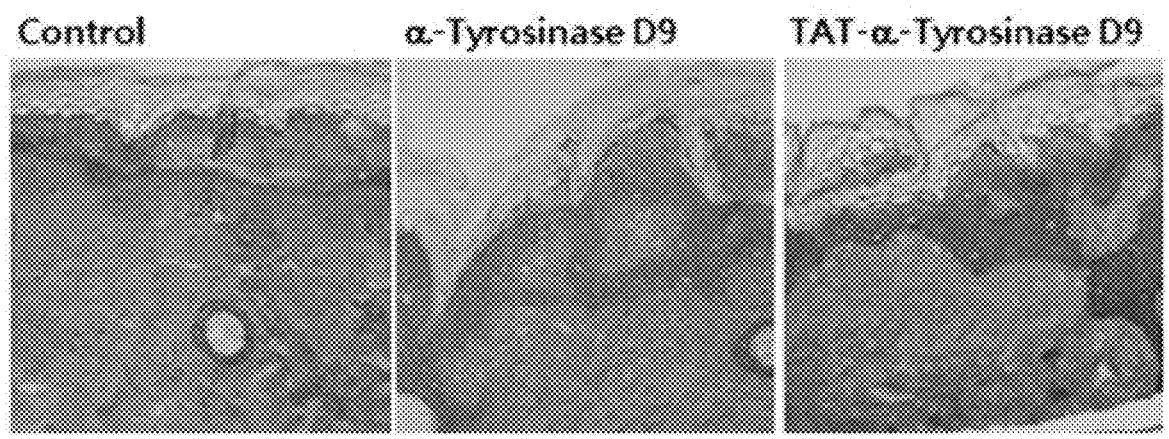

SEQUENCE LISTING

<160> NUMBER OF SEQ ID NOS: 8

<210> SEQ ID NO 1
<211> LENGTH: 13
<212> TYPE: PRT
<213> ORGANISM: Artificial Sequence
<220> FEATURE:
<223> OTHER INFORMATION: light chain CDR1

<400> SEQUENCE: 1

Thr Gly Ser Ser Ser Asn Ile Gly Asn Asn Asp Val Thr
1               5                   10

<210> SEQ ID NO 2
<211> LENGTH: 4
<212> TYPE: PRT
<213> ORGANISM: Artificial Sequence
<220> FEATURE:
<223> OTHER INFORMATION: light chain CDR2

<400> SEQUENCE: 2

Asn Asp Asn Gln
1

<210> SEQ ID NO 3
<211> LENGTH: 9
<212> TYPE: PRT
<213> ORGANISM: Artificial Sequence
<220> FEATURE:
<223> OTHER INFORMATION: light chain CDR3

<400> SEQUENCE: 3

Gly Thr Trp Asp Ser Ser Leu Ser Gly
1               5

<210> SEQ ID NO 4
<211> LENGTH: 5
<212> TYPE: PRT
<213> ORGANISM: Artificial Sequence
<220> FEATURE:
<223> OTHER INFORMATION: heavy chain CDR1

<400> SEQUENCE: 4

Ser Tyr Asp Met Ser
1               5

<210> SEQ ID NO 5
<211> LENGTH: 9
<212> TYPE: PRT
<213> ORGANISM: Artificial Sequence
<220> FEATURE:
<223> OTHER INFORMATION: heavy chain CDR2

<400> SEQUENCE: 5

Gly Ile Ser His Gly Gly Ser Ser Thr
1               5

<210> SEQ ID NO 6
<211> LENGTH: 19
<212> TYPE: PRT
<213> ORGANISM: Artificial Sequence
<220> FEATURE:
<223> OTHER INFORMATION: heavy chain CDR3

<400> SEQUENCE: 6

Arg Asp Ile Ile His Cys Asn Pro Leu Trp Cys Ser Tyr Ala Asp Gly
1               5                   10                  15

```
Met Asp Val

<210> SEQ ID NO 7
<211> LENGTH: 11
<212> TYPE: PRT
<213> ORGANISM: Artificial Sequence
<220> FEATURE:
<223> OTHER INFORMATION: TAT peptide

<400> SEQUENCE: 7

Tyr Gly Arg Lys Lys Arg Arg Gln Arg Arg Arg
1               5                   10

<210> SEQ ID NO 8
<211> LENGTH: 33
<212> TYPE: DNA
<213> ORGANISM: Artificial Sequence
<220> FEATURE:
<223> OTHER INFORMATION: TAT peptide

<400> SEQUENCE: 8
tatggccgca aaaaacgccg ccagcgccgc cgc                                  33
```

ANTI-TYROSINASE ANTIBODY FOR INHIBITING TYROSINASE AND USE THEREOF

CROSS REFERENCE TO PRIOR APPLICATIONS

This application is the 35 U.S.C. 371 national stage of international application PCT/KR2019/017719 filed on Dec. 13, 2019; which claims priority to Korean application 10-2019-0096864 filed on Aug. 8, 2019. The entire contents of each of the above-identified applications are hereby incorporated by reference.

TECHNICAL FIELD

The present invention relates to an anti-tyrosinase antibody for inhibiting tyrosinase and use thereof.

BACKGROUND ART

Human skin color varies according to various factors, in particular, season, race, and gender, and is mainly determined by the amounts of melanin, carotene, and hemoglobin, of which melanin acts as the most decisive factor. Melanin is synthesized in melanocytes present in the basal layer of the skin and metastasizes to surrounding keratinocytes to give human skin color. It is known that in the case that melanin is abnormally low, skin lesions such as vitiligo are induced, and in the case that it is excessively produced, spots and blemishes are formed. Melanin is produced by the action of tyrosinase on tyrosine, an amino acid. Since tyrosinase is more activated by ultraviolet rays, the skin turns black when exposed to a lot of sunlight. Therefore, the basic mechanism of drugs for development of whitening cosmetics to prevent pigmentation may include inhibition of the activity of tyrosinase, inhibition of the production of tyrosinase, inhibition of a mediator that promotes the production of melanin, reduction of the produced melanin and inhibition of photooxidation, promotion of excretion of melanin, and UV protection. Among these, one of the simplest and most effective ways to obtain a skin whitening effect is inhibition of the activity of tyrosinase.

Although skin whitening through inhibition of the activity of tyrosinase is being actively researched, research on an antibody for inhibiting tyrosinase is still lacking.

DISCLOSURE

Technical Problem

An object of the present invention is to provide an anti-tyrosinase antibody for inhibiting tyrosinase or an antigen-binding fragment thereof.

Another object of the present invention is to provide a fusion anti-tyrosinase antibody or an antigen-binding fragment thereof in which a TAT peptide is further bound to the anti-tyrosinase antibody or antigen-binding fragment thereof.

Still another object of the present invention is to provide a nucleic acid molecule encoding the antibody or antigen-binding fragment thereof, a recombinant expression vector containing the nucleic acid molecule, and a cell transformed with the recombinant expression vector.

Still another object of the present invention is to provide a composition for detecting a tyrosinase antigen containing the antibody or antigen-binding fragment thereof as an active ingredient.

Still another object of the present invention is to provide a cosmetic composition for skin whitening or a health functional food composition containing the antibody or antigen-binding fragment thereof as an active ingredient.

Still another object of the present invention is to provide a pharmaceutical composition for preventing or treating skin pigmentation disorders or a composition for diagnosing skin pigmentation disorders containing the antibody or antigen-binding fragment thereof as an active ingredient, or a method for providing information necessary for diagnosing skin pigmentation disorders.

Technical Solution

In order to achieve the above objects, the present invention provides an anti-tyrosinase antibody including a light chain variable region including a light chain CDR1 consisting of an amino acid sequence represented by SEQ ID NO: 1, a light chain CDR2 consisting of an amino acid sequence represented by SEQ ID NO: 2, and a light chain CDR3 consisting of an amino acid sequence represented by SEQ ID NO: 3; and a heavy chain variable region including a heavy chain CDR1 consisting of an amino acid sequence represented by SEQ ID NO: 4, a heavy chain CDR2 consisting of an amino acid sequence represented by SEQ ID NO: 5, and a heavy chain CDR3 consisting of an amino acid sequence represented by SEQ ID NO: 6, or an antigen-binding fragment thereof.

In addition, the present invention provides a fusion anti-tyrosinase antibody or an antigen-binding fragment thereof in which a TAT peptide represented by SEQ ID NO: 7 is further bound to the antibody or antigen-binding fragment thereof.

In addition, the present invention provides a nucleic acid molecule encoding the antibody or antigen-binding fragment thereof.

In addition, the present invention provides a recombinant expression vector containing the nucleic acid molecule.

In addition, the present invention provides a cell transformed with the recombinant expression vector.

In addition, the present invention provides a composition for detecting a tyrosinase antigen containing the antibody or antigen-binding fragment thereof as an active ingredient.

In addition, the present invention provides a cosmetic composition for skin whitening containing the antibody or antigen-binding fragment thereof as an active ingredient.

In addition, the present invention provides a health functional food composition for skin whitening containing the antibody or antigen-binding fragment thereof as an active ingredient.

In addition, the present invention provides a pharmaceutical composition for preventing or treating skin pigmentation disorders containing the antibody or antigen-binding fragment thereof as an active ingredient.

In addition, the present invention provides a composition for diagnosing skin pigmentation disorders containing the antibody or antigen-binding fragment thereof as an active ingredient.

In addition, the present invention provides a method for providing information necessary for diagnosing a skin pigmentation disorder including contacting the antibody or antigen-binding fragment thereof with a sample isolated from an individual suspected of having a skin pigmentation disorder; and detecting a tyrosinase protein from the sample through an antigen-antibody reaction.

Advantageous Effects

The present invention relates to an anti-tyrosinase antibody for inhibiting tyrosinase and a use thereof, and more particularly, to an anti-tyrosinase antibody including heavy chain CDRs and light chain CDRs of specific sequences, or an antigen-binding fragment thereof. The anti-tyrosinase antibody is expected to be effectively utilized for improving skin whitening or treating skin pigmentation disorders by inhibiting tyrosinase activity.

BRIEF DESCRIPTIONS OF THE DRAWINGS

FIG. 1 shows results of an ELISA assay for selecting α-tyrosinase scFv antibodies.

FIG. 2 shows a result of reproducibility verification of the ELISA assay.

FIG. 3 shows size and protein purity results through SDS-PAGE after purification of a cell-permeable α-tyrosinase scFv protein.

FIG. 4 shows results of inhibition of tyrosinase enzyme activity of the cell-permeable α-tyrosinase scFv protein.

FIG. 5 shows results of pig skin permeability of the cell-permeable α-tyrosinase scFv protein by DAB staining.

BEST MODE

The present invention provides an anti-tyrosinase antibody including a light chain variable region including a light chain CDR1 consisting of an amino acid sequence represented by SEQ ID NO: 1, a light chain CDR2 consisting of an amino acid sequence represented by SEQ ID NO: 2, and a light chain CDR3 consisting of an amino acid sequence represented by SEQ ID NO: 3; and a heavy chain variable region including a heavy chain CDR1 consisting of an amino acid sequence represented by SEQ ID NO: 4, a heavy chain CDR2 consisting of an amino acid sequence represented by SEQ ID NO: 5, and a heavy chain CDR3 consisting of an amino acid sequence represented by SEQ ID NO: 6, or an antigen-binding fragment thereof.

In addition, the present invention provides the present invention provides a fusion anti-tyrosinase antibody or an antigen-binding fragment thereof in which a TAT peptide represented by SEQ ID NO: 7 is further bound to the antibody or antigen-binding fragment thereof.

CDRs consisting of the amino acids represented by SEQ ID NO: 1 to SEQ ID NO: 6 are described in Table 1.

In addition, the amino acid sequence of the TAT peptide used in the present invention is "YGRKKRRQRRR" (SEQ ID NO: 7), and the nucleotide sequence of the TAT peptide is "TAT GGC CGC AAA AAA CGC CGC CAG CGC CGC CGC" (SEQ ID NO: 8).

As used herein, the term "antibody" refers to a protein molecule serving as a receptor that specifically recognizes an antigen, including an immunoglobulin molecule having immunological reactivity with a specific antigen. For example, the antibody may include a monoclonal antibody, a polyclonal antibody, a full-length antibody, and an antibody fragment. The term "antibody" may also include a bivalent or bispecific molecule (for example, a bispecific antibody), a diabody, a triabody, or a tetrabody.

As used herein, the term "monoclonal antibody" refers to an antibody molecule having a single molecular composition obtained from a population of substantially identical antibodies. Such a monoclonal antibody exhibits single binding and affinity for a particular epitope, unlike a polyclonal antibody that can bind to multiple epitopes. As used herein, the term "full-length antibody" has a structure having two full-length light chains and two full-length heavy chains, and each light chain is connected to the heavy chain by a disulfide bond. A heavy chain constant region has gamma (γ), mu (μ), alpha (α), delta (δ), and epsilon (ε) types and subclasses gamma 1 (γ1), gamma 2 (γ2), gamma 3 (γ3), gamma 4 (γ4), alpha 1 (α1), and alpha 2 (α2). A light chain constant region has kappa (κ) and lambda (λ) types. IgG includes IgG1, IgG2, IgG3, and IgG4 as subtypes.

As used herein, the term "heavy chain" may include a full-length heavy chain including a variable region VH including an amino acid sequence having a sufficient variable region sequence to confer specificity to an antigen and three constant regions CH1, CH2 and CH3, and a fragment thereof. In addition, as used herein, the term "light chain" may include a full-length light chain including a variable region VL including an amino acid sequence having a sufficient variable region sequence to confer specificity to an antigen and a constant region CL, and a fragment thereof.

As used herein, the terms "fragment", "antibody fragment", and "antigen-binding fragment" are used interchangeably to refer to any fragment of the antibody of the present invention that retains an antigen-binding function of the antibody. Exemplary antigen-binding fragments include, but are not limited to, Fab, Fab', F(ab')2, and Fv.

The antibody or antigen-binding fragment thereof of the present invention may include not only the sequence of the antibody described herein, but also biological equivalents thereof to the extent that they can exhibit an ability to specifically bind to tyrosinase. For example, additional changes may be made to the amino acid sequence of the antibody to further improve the binding affinity and/or other biological properties of the antibody. Such a modification includes, for example, deletion, insertion and/or substitution of amino acid sequence residues of the antibody. Such an amino acid variation is made based on relative similarity of an amino acid side chain substituent, such as hydrophobicity, hydrophilicity, charge, and size. Analysis of the size, shape, and type of the amino acid side chain substituent shows that arginine, lysine, and histidine are all positively charged residues; alanine, glycine, and serine have similar sizes; and phenylalanine, tryptophan, and tyrosine have similar shapes. Therefore, based on the foregoing, arginine, racine, and histidine; alanine, glycine, and serine; and phenylalanine, tryptophan, and tyrosine can be said to be biologically functional equivalents.

The present invention also provides a nucleic acid molecule encoding the antibody or antigen-binding fragment thereof.

As used herein, the term "nucleic acid molecule" has a meaning comprehensively including DNA (gDNA and cDNA) and RNA molecules. Nucleotides, which are basic building blocks of the nucleic acid molecule, include not only natural nucleotides, but also analogs in which sugar or base sites are modified. The sequence of the nucleic acid molecule encoding the heavy and light chain variable regions of the invention may be modified, including additions, deletions, or non-conservative or conservative substitutions of nucleotides.

In addition, the present invention provides a recombinant expression vector containing the nucleic acid molecule.

As used herein, the term "vector" refers to a self-replicating DNA molecule used to carry a clonal gene (or another piece of clonal DNA).

As used herein, the term "expression vector" refers to a recombinant DNA molecule containing a desired coding sequence and an appropriate nucleic acid sequence essential for expressing a coding sequence operably linked in a specific host organism. The expression vector may preferably include one or more selectable markers. The marker is a nucleic acid sequence having characteristics that can be selected by conventional chemical methods, and includes all genes that can distinguish transformed cells from non-transformed cells. Examples include, but are not limited to, antibiotic resistance genes such as Ampicillin, Kanamycin, Geneticin (G418), Bleomycin, Hygromycin, and Chloramphenicol, and those skilled in the art may appropriately select one or more.

To express the DNA sequence of the present invention, any of a wide variety of expression control sequences may be used in the vector. Examples of useful expression control sequences may include early and late promoters of SV40 or adenovirus, promoters and enhancers of CMV, LTR of retrovirus, lac system, trp system, TAC or TRC system, T3 and T7 promoters, major operator and promoter regions of phage lambda, regulatory regions of fd coding proteins, promoters for 3-phosphoglycerate kinase or other glycolytic enzymes, promoters of the phosphatase such as Pho5, yeast alpha-crossing system promoters, and other sequences of structure and induction known to regulate the expression of genes in prokaryotic or eukaryotic cells or viruses thereof, and various combinations thereof.

The vector expressing the antibody of the present invention may be a vector system in which a light chain and a heavy chain are simultaneously expressed in one vector or a system in which a light chain and a heavy chain are each expressed in separate vectors. For the latter, the two vectors are introduced into a host cell through co-transformation and targeted transformation. Co-transformation is a method of selecting cells expressing both light and heavy chains after simultaneously introducing each vector DNA encoding the light and heavy chains into the host cell. Targeted transformation is a method for finally selecting cells expressing both the light chain and the heavy chain by selecting cells transformed with a vector containing the light chain (or heavy chain) and re-transforming the selected cells expressing the light chain with a vector containing the heavy chain (or light chain).

In addition, the present invention provides a cell transformed with the recombinant expression vector.

Cells capable of stably and continuously cloning and expressing the vector of the present invention may be any host cells known in the art, and may include, but are not limited to, prokaryotic host cells such as *Escherichia coli*, *Bacillus* genus strains such as *Bacillus subtilis* and *Bacillus thuringiensis*, *Streptomyces*, *Pseudomonas* (for example, *Pseudomonas putida*), *Proteus mirabilis*, or *Staphylococcus* (for example, *Staphylococcus carnosus*).

According to a method for producing the antibody or antigen-binding fragment thereof, the transformed cell may be cultured according to an appropriate medium and culture conditions known in the art. A person skilled in the art can easily adjust and use a culture process according to a selected strain. Cell culture is divided into suspension culture and adherent culture according to cell growth methods, and batch, fed-batch, and continuous culture according to culture methods. The medium used for culture should suitably satisfy the requirements of a particular strain.

In addition, the present invention provides a composition for detecting a tyrosinase antigen containing the antibody or antigen-binding fragment thereof as an active ingredient.

In addition, the present invention provides a cosmetic composition for skin whitening containing the antibody or antigen-binding fragment thereof as an active ingredient.

The cosmetic composition may include, in addition to the active ingredient, conventional adjuvants such as stabilizers, solubilizers, vitamins, pigments, and fragrances, and carriers.

The cosmetic composition may be prepared in any formulation conventionally prepared in the art, and may have a formulation selected from the group consisting of skin external ointment, cream, softening lotion, nutrient lotion, pack, essence, hair tonic, shampoo, rinse, hair conditioner, hair treatment, gel, skin lotion, skin softener, skin toner, astringent, lotion, milk lotion, moisture lotion, nourishing lotion, massage cream, nourishing cream, eye cream, moisture cream, hand cream, foundation, nourishing essence, sunscreen, soap, cleansing foam, cleansing lotion, cleansing cream, body lotion, and body cleanser, but not limited thereto. The composition of each of these formulations may contain various bases and additives necessary and appropriate for preparation of the formulation, and the types and amounts of these components can be easily selected by those skilled in the art.

In the case that the formulation is a paste, cream, or gel, animal oil, vegetable oil, wax, paraffin, starch, tracanth, cellulose derivatives, polyethylene glycol, silicone, bentonite, silica, talc, or zinc oxide may be used as a carrier component.

In the case that the formulation is a powder or spray, lactose, talc, silica, aluminum hydroxide, calcium silicate, or polyamide powder may be used as the carrier component. In particular, in the case of the spray, a propellant such as chlorofluorohydrocarbon, propane/butane, or dimethyl ether may be further included.

In the case that the formulation is a solution or emulsion, a solvent, solubilizer or emulsifier is used as the carrier component, for example, including water, ethanol, isopropanol, ethyl carbonate, ethyl acetate, benzyl alcohol, benzyl benzoate, propylene glycol, 1,3-Butylglycol oil, glycerol fatty ester, polyethylene glycol, or fatty acid ester of sorbitan.

In the case that the formulation is a suspension, as the carrier component, a liquid diluent such as water, ethanol, or propylene glycol, a suspending agent such as ethoxylated isostearyl alcohol, polyoxyethylene sorbitol ester, and polyoxyethylene sorbitan ester, microcrystalline cellulose, aluminum metahydroxide, bentonite, agar, or tragacanth may be used.

In addition, the present invention provides a health functional food composition for skin whitening containing the antibody or antigen-binding fragment thereof as an active ingredient.

The health functional food composition may be provided in the form of powder, granule, tablet, capsule, syrup, beverage, or pill, and may be used together with other food or food additives in addition to the composition according to the present invention as an active ingredient. The health functional food composition may be used appropriately according to a conventional method. The mixing amount of the active ingredient may be appropriately determined according to the intended use thereof, for example, prophylactic, health, or therapeutic treatment.

The effective dose of the antibody or antigen-binding fragment thereof contained in the health functional food composition may be equivalent to the effective dose of the pharmaceutical composition. However, in the case of long-term intake for health and hygiene or health control, it may be less than the above range, and it is certain that the active ingredient can be used in an amount beyond the above range because the active ingredient has no problem in terms of safety.

The type of health functional food is not particularly limited, and may include meat, sausage, bread, chocolate, candy, snacks, confectionery, pizza, ramen, other noodles, gum, dairy products including ice cream, various soups, beverages, tea, drinks, alcoholic beverages, and vitamin complexes, for example.

In addition, the present invention provides a pharmaceutical composition for preventing or treating a skin pigmentation disorder containing the antibody or antigen-binding fragment thereof as an active ingredient.

Specifically, the skin pigmentation disorder may be melasma, freckles, black spots, nevus, pigmentation caused by drugs, post-inflammatory pigmentation, or hyperpigmentation occurring in dermatitis, but is not limited thereto.

The pharmaceutical composition of the present invention may further include a pharmaceutically acceptable carrier. The pharmaceutically acceptable carrier is commonly used in the formulation, and may include, but not limited thereto, lactose, dextrose, sucrose, sorbitol, mannitol, starch, acacia gum, calcium phosphate, alginate, gelatin, calcium silicate, microcrystalline cellulose, polyvinylpyrrolidone, cellulose, water, syrup, methylcellulose, methylhydroxybenzoate, propylhydroxybenzoate, talc, magnesium stearate, and mineral oil. The pharmaceutical composition of the present invention may further include a lubricant, a wetting agent, a sweetening agent, a flavoring agent, an emulsifying agent, a suspending agent, a preservative, and the like, in addition to the above components.

The pharmaceutical composition of the present invention may be administered orally or parenterally, and the parenteral administration may be intravenous injection, subcutaneous injection, intramuscular injection, intraperitoneal injection, endothelial administration, topical administration, intranasal administration, intrapulmonary administration, or rectal administration. In the case of the oral administration, oral compositions may be formulated to coat an active agent or to protect it from degradation in the stomach because a protein or peptide is digested. The composition of the present invention may administered by any device capable of transporting the active agent to a target cell.

A suitable dosage of the pharmaceutical composition of the present invention varies depending on factors such as formulation method, administration mode, and age, weight, sex, pathology, food, administration time, administration route, excretion rate, and response sensitivity of the patient. An ordinarily skilled physician can easily determine and prescribe an effective dosage for desired treatment or prevention.

The pharmaceutical composition of the present invention may be prepared in unit dosage form by formulating using the pharmaceutically acceptable carrier and/or excipient or prepared by being introduced into a multi-dose container, according to a method that can be easily carried out by a person skilled in the art to which the present invention pertains. In this case, the formulation may be in the form of a solution, suspension, or emulsion in an oil or aqueous medium, or may be in the form of an extract, powder, suppository, granule, tablet, or capsule, and may additionally include a dispersant or stabilizer.

The composition of the present invention may be administered as an individual therapeutic agent or in combination with other therapeutic agents, and may be administered sequentially or simultaneously with conventional therapeutic agents.

In addition, the present invention provides a composition for diagnosing a skin pigmentation disorder containing the antibody or antigen-binding fragment thereof as an active ingredient.

Specifically, the skin pigmentation disorder may be melasma, freckles, black spots, nevus, pigmentation caused by drugs, post-inflammatory pigmentation, or hyperpigmentation occurring in dermatitis, but is not limited thereto.

In addition, the present invention provides a method for providing information necessary for diagnosing a skin pigmentation disorder including contacting the antibody or antigen-binding fragment thereof with a sample isolated from an individual suspected of having a skin pigmentation disorder; and detecting a tyrosinase protein from the sample through an antigen-antibody reaction.

Specifically, the skin pigmentation disorder may be melasma, freckles, black spots, nevus, pigmentation caused by drugs, post-inflammatory pigmentation, or hyperpigmentation occurring in dermatitis, but is not limited thereto.

The step of detecting the tyrosinase protein through the antigen-antibody reaction may be performed by any methods capable of detecting the tyrosinase protein by measuring antigen-antibody binding. Such methods are known in the art and may include, but not limited thereto, western blot, ELISA, radioimmunoassay, radioimmunodiffusion, immunofluorescence, immunoblot, Oucreroni immunodiffusion, rocket immunoelectrophoresis, tissue immunostaining, immunoprecipitation assay, complement fixation assay, immunochromatographic assay, FACS, and protein chip, for example.

A tool or reagent used for immunological assay of the antigen-antibody reaction may include a suitable carrier or support, a label capable of generating a detectable signal, a solubilizer, a detergent, and a stabilizer. Suitable carriers may include, but are not limited to, a substrate capable of measuring enzymatic activity in the case that labeling material is an enzyme, an appropriate buffer solution, a secondary antibody labeled with chromogenic enzyme or fluorescent substance, a chromogenic substrate, and a reaction terminator.

MODES FOR CARRYING OUT INVENTION

Hereinafter, the present invention will be described in more detail through examples. These examples are merely for illustrating the present invention in more detail, and it will be apparent to those skilled in the art that the scope of the present invention is not limited by these examples according to the gist of the present invention.

<Example 1> α-Tyrosinase scFv Antibody Selection

1. Implementation of Bio-Panning

Bio-panning was performed using OPAL library with a diversity of $7.6 \times 10^9$. 5 μg of tyrosinase antigen was immobilized on an epoxy magnetic bead and an input phage was reacted. The output titer was measured by elution of the phage reacted with the antigen. By measuring the input and output titers every time repeatedly, bio-panning information was obtained and it was checked whether or not the bio-panning was performed normally. For each repetition, a phage of $2 \times 10^{12}$ cfu/ml≥was used as the input phage. The output was 1st—$1.7 \times 10^6$, 2nd—$3.65 \times 10^6$, and 3rd—$4.68 \times 10^8$ cfu/ml, which was found to be amplified as the bio-panning progressed. Therefore, it was determined that the bio-panning proceeded normally.

2. ELISA Assay

The ELISA assay was performed for selection of a highly sensitive and highly specific antibodies. The obtained phage was infected with *E. coli* and spread on an LB plate to which antibiotics were added. After culturing in an incubator at 30° C. for 16 hours, resulting colonies were randomly collected.

Each colony was cultured in LB medium and treated with IPTG to express scFv, and *E. coli* was lysed to obtain a soluble fraction, followed by ELISA. First, 30 ng of the tyrosinase antigen was fixed in a 96 well ELISA plate, and blocked with PBS containing 3% BSA. After 1 hour, the cell lysate obtained above was treated and reacted at 37° C. for 2 hours. After washing the plate 3 times with PBS containing 0.1% Tween20, the HRP-conjugated anti-HA antibody was diluted 1:1000 in a blocking solution and reacted at 37° C. for 1 hour. After washing the plate 5 times with PBS containing 0.1% Tween20, it was colored with TMB substrate, and the scFv antibody bound to the antigen was measured with an ELISA leader. 96 antibodies were analyzed, OD 0.4 was arbitrarily set as a positive guideline and 0.1 as a negative guideline, and 11 types were selected (FIG. 1).

<Example 2> α-Tyrosinase scFv Antibody Sequence Analysis

Individual clones were selected through sequencing of 11 positive clones of tyrosinase scFv selected through the ELISA assay. Since there is a possibility that overlapping clones exist among the positive clones previously selected, sequencing was required. As a result of sequencing, it was determined that two of the 11 positive clones were individual clones.

<Example 3> Purification and Sensitivity Analysis of Selected α-Tyrosinase Antibody 1. Purification of α-Tyrosinase scFv Antibody One previously selected α-tyrosinase scFv antibody was purified (Table 1). ER2738 *E. coli* cells in which one type of clone had been transformed were cultured in 500 ml of SB media, and then the cells were lysed using 1×TES buffer. The cell lysate was reacted with 0.5 ml Ni beads and eluted using imidazole.

TABLE 1

| Target | Clone | Light chain CDR sequence | | | Heavy chain CDR sequence | | |
|---|---|---|---|---|---|---|---|
| | | CDR1 | CDR2 | CDR3 | CDR1 | CDR2 | CDR3 |
| Tyrosinase | D9 | TGSSSNIGNNDVT | NDNQ | GTWDSSLSG | SYDMS | GISHGGSST | RDIIHCNPLWCSYADGMDV |

2. Sensitivity Analysis of Purified α-Tyrosinase scFv Antibody

Sensitivity analysis was performed using the purified α-tyrosinase scFv antibody. The ELISA assay was used for the sensitivity analysis. First, various concentrations of the tyrosinase antigen were immobilized on an ELISA plate and then treated with the α-tyrosinase scFv antibody at 10 μg/ml. The assay was performed using HRP conjugated anti-HA antibody diluted 1:1000. The assay was performed with EC50-1368 ng/ml, LOD-12.5 ng/ml (FIG. 2).

<Example 4> Preparation of Cell-Permeable α-Tyrosinase scFv

1. Preparation of TAT-α-Tyrosinase scFv Construct

A PCR product was produced in which a restriction enzyme site and TAT were inserted using the previously selected scFv primer. 30 μl of each PCR product was treated with 4 μl of buffer 3.1, 1 μl of EcoRI, 1 μl of XhoI, and 4 μl of distilled water, and reacted at 37° C. for 1 hour. Then, the DNA was isolated and an insert to be inserted into a vector was obtained. A pET28a(+) vector was transformed into DH5a competent cells, and then the cells were spread on an LB plate added with kanamycin and cultured at 37° C. for 16 hours. The next day, colonies were collected and inoculated into LB media added with kanamycin, and incubated at 37° C. for 16 hours. The next day, after separating the vector using a mini-prep kit, 30 μl of the vector was treated with 4 μl of buffer 3.1, 1 μl of EcoRI, 1 μl of XhoI, 1 μl of CIP, and 3 μl of distilled water, reacted at 37° C. for 1 hour, and then purified. The concentrations of the purified vector and insert were measured with NanoDrop, and ligation was performed at room temperature for 16 hours using T4 ligase for each ratio of the vector and insert. After the ligation, DH5a was transformed and spread on an LB plate added with kanamycin, and cultured at 37° C. for 16 hours. The next day, colonies were collected and inoculated into LB media added with kanamycin, and incubated at 37° C. for 16 hours. The next day, to check whether or not the insert was inserted, plasmid was separated and restricted with EcoRI and XhoI. The band was identified by electrophoresis on 1 agarose gel.

2. Purification of TAT-α-Tyrosinase scFv Antibody

The cloned TAT-α-tyrosinase scFv antibody clone was transformed into a BL21 (DE3) *E. coli* host, and transformant was induced with 0.5 mM IPTG. The scFv antibody was suspended in lysis buffer (50 mM Tris-HCl, pH 7.5, 150 mM NaCl), disrupted using an ultrasonicator, and centrifuged to obtain a supernatant. Protein was purified using a resin having an affinity for Ni-NTA. It was determined that expression was well through SDS-PAGE analysis. The protein size was found to be about 30 kDa (FIG. 3).

<Example 5> Cytotoxicity Test of Cell-Permeable Anti-Tyrosinase scFv

In order to examine cytotoxicity of the TAT-α-tyrosinase scFv antibody, B16F10 cells, mouse-derived malignant melanoma cells, were cultured in a $CO_2$ incubator at 37° C. After the culture, the cells were treated with the TAT-α-tyrosinase scFv antibody at different concentrations (0.1, 1, 5, 10, 50, 100 ppm), and then further cultured under the same culture conditions. After the culture, MTT{3-(4,5-Dimethylthiazol-2-yl)-2,5-Diphenyltetrazolium Bromide} solution was added and cultured. After that, the culture solution was removed, and DMSO (dimethyl sulfoxide) was added and shaken moderately. Then, absorbance was measured at 570 nm using an ELISA Reader system, and the values are shown in Table 2. As shown in Table 2, in the case of treating with TAT-α-tyrosinase scFv at the concentrations of 0.1, 1, 5, 10, 50, and 100 ppm, it was determined that there was little change in cell shape transformation and cell viability of the malignant melanoma cells up to the concentration of 100 ppm. Therefore, it was determined that TAT-α-tyrosinase scFv is a material without cytotoxicity up to the concentration of 100 ppm.

TABLE 2

| Concentration (ppm) | Positive Control Arbutin Average | Error | Example 5 TAT-α-tyrosinase D9 Average | Error |
|---|---|---|---|---|
| 0 | 100.0 | 3.1 | 100.0 | 9.6 |
| 0.1 | 97.6 | 5.8 | 101.0 | 3.3 |
| 1 | 97.0 | 5.6 | 108.9 | 7.0 |
| 5 | 83.5 | 3.3 | 104.9 | 10.8 |
| 10 | 89.3 | 2.3 | 94.2 | 3.8 |
| 50 | 82.4 | 8.1 | 98.1 | 5.7 |
| 100 | 57.7 | 2.1 | 102.2 | 3.0 |

<Example 6> Test for Tyrosinase Activity Inhibitory Effect of Cell-Permeable Anti-Tyrosinase scFv For TAT-α-tyrosinase scFv, an effect on tyrosinase activity involved in the production of melanin pigment was investigated. 100 ul of 0.1 M phosphate buffer (pH 6.8) was added to 5 ug of TAT-α-tyrosinase scFv, 10 ul of 300 unit/ml mushroom tyrosinase was added, 20 ul of 1.5 mM L-tyrosine solution was added, and reaction was carried out at 37° C. for 20 minutes. Then, the absorbance was measured at 490 nm with the ELISA Reader system, and the values are shown in FIG. 4. As shown in FIG. 4, it was determined that TAT-α-tyrosinase scFv inhibited the tyrosinase activity and exhibited a similar effect to arbutin at the same concentration.

<Example 7> Test for Melanin Production Inhibitory Effect of Cell-Permeable Anti-Tyrosinase scFv To determine an inhibitory effect of the TAT-α-tyrosinase scFv antibody on melanin production in cells, B16F10 cell lines were treated with the TAT-α-tyrosinase scFv antibody and then the produced intracellular melanin content was measured. B16F10 cells, which are malignant melanoma cells, were cultured at 37° C. in the $CO_2$ incubator. Thereafter, the cells were treated with 10 ppm of the TAT-α-tyrosinase scFv antibody and 100 ppm of arbutin as a positive control, followed by further culture under the same culture conditions. After the culture, each well was washed with PBS and 130 ul of 1 N NaOH solution was added to dissolve it at 60° C. for 1 hour. Then, the absorbance was measured at 475 nm with the ELISA Reader system, and the values are shown in Table 3. As shown in Table 3, it was determined that TAT-α-tyrosinase scFv inhibited melanin production and exhibited a similar effect to arbutin.

TABLE 3

| | Sample | Melanin biosynthesis amount (% of control) Average | Error |
|---|---|---|---|
| Negative control | Control | 100.0 | 1.1 |
| Positive control | Arbutin | 66.1 | 0.3 |
| Example 7 | TAT-α-tyrosinase D9 | 65.8 | 0.2 |

<Example 8> Test for Reactive Oxygen Species Inhibitory Effect of Cell-Permeable Anti-Tyrosinase scFv In order to determine the inhibitory effect of the TAT-α-tyrosinase scFv antibody on reactive oxygen species in cells, the B16F10 cell lines were treated with the TAT-α-tyrosinase scFv antibody, and then the content of intracellular reactive oxygen species was measured using fluorescence staining. B16F10 cells, which are malignant melanoma cells, were cultured in the $CO_2$ incubator at 37° C. Thereafter, the cells were treated with 100 ppm of the TAT-α-tyrosinase scFv antibody and 100 ppm of arbutin as a positive control, and then further cultured under the same culture conditions. After the culture, 0.2 mM hydrogen peroxide was added to each well, and then cultured for 2 hours. Carboxy-$H_2$DCF-DA was added and reaction was carried out at 37° C. for 30 minutes. After washing with PBS, fluorescence was measured with the ELISA Reader system at 475/535 nm by re-addition of PBS, and the values are shown in Table 4. As shown in Table 4, it was determined that TAT-α-tyrosinase scFv inhibited ROS generation and exhibited a superior effect than arbutin at the same concentration.

TABLE 4

| | Sample | ROS (fold of control) | | | |
|---|---|---|---|---|---|
| | | non treat control | | 0.2 mM $H_2O_2$ | |
| | | Average | Error | Average | Error |
| Negative control | Control | 1.00 | 0.02 | 1.42 | 0.03 |
| Positive control | Arbutin | 0.82 | 0.02 | 1.29 | 0.05 |
| Example 8 | TAT-α-tyrosinase D9 | 0.83 | 0.04 | 1.16 | 0.03 |

<Example 9> Skin Permeation Analysis of Cell-Permeable Anti-Tyrosinase scFv

Skin permeation of TAT-α-tyrosinase scFv was determined by tissue staining using pig skin. Pig skin was treated with 10 ug of the TAT-α-tyrosinase scFv antibody and cultured for 16 hours in the $CO_2$ incubator at 37° C. After fixing the pig skin with 4% formaldehyde, a paraffin block was prepared, and the tissue was excised at 5 μm using a microtome. After that, the tissue was mounted on a slide, the paraffin was removed, and the tissue section was blocked for 30 minutes after hydration. Anti-His HRP antibody was reacted with the blocked tissue at room temperature for 1 hour. After washing with PBST, it was reacted with a DAB-chromogen solution for 5 minutes, stained with H&E staining technique, and observed with an optical microscope. FIG. 5 shows a result of comparing the skin permeability of α-tyrosinase scFv and TAT-α-tyrosinase scFv. As shown in FIG. 5, it was confirmed that α-tyrosinase scFv was not delivered into the pig skin tissue at all, whereas TAT-α-tyrosinase scFv had an efficient skin delivery ability.

Although specific parts of the present invention have been described in detail above, these specific descriptions are merely preferred example embodiments for those skilled in the art, and it is clear that the scope of the present invention is not limited thereto. Accordingly, the substantial scope of the present invention should be defined by the appended claims and their equivalents.

What is claimed is:

1. An anti-tyrosinase antibody comprising a light chain variable region comprising a light chain CDR1 consisting of an amino acid sequence represented by SEQ ID NO: 1, a light chain CDR2 consisting of an amino acid sequence represented by SEQ ID NO: 2, and a light chain CDR3 consisting of an amino acid sequence represented by SEQ ID NO: 3; and a heavy chain variable region comprising a heavy chain CDR1 consisting of an amino acid sequence represented by SEQ ID NO: 4, a heavy chain CDR2 consisting of an amino acid sequence represented by SEQ ID NO: 5, and a heavy chain CDR3 consisting of an amino acid sequence represented by SEQ ID NO: 6, or an antigen-binding fragment thereof.

2. A fusion anti-tyrosinase antibody or antigen-binding fragment thereof in which a TAT peptide represented by SEQ ID NO: 7 is further bound to the antibody or antigen-binding fragment thereof of claim 1.

3. A method of improving skin whitening, comprising:
providing a cosmetic composition comprising the antibody or antigen-binding fragment thereof of claim 1 as an active ingredient; and
administering the cosmetic composition to a subject.

4. A method of improving skin whitening, comprising:
providing a cosmetic composition comprising the antibody or antigen-binding fragment thereof of claim 2 as an active ingredient; and
administering the cosmetic composition to a subject.

* * * * *